United States Patent
Mäntylä et al.

(10) Patent No.: US 10,444,143 B2
(45) Date of Patent: Oct. 15, 2019

(54) OPTICAL MULTI-CHANNEL MEASUREMENT UNIT, OPTICAL MULTI-CHANNEL DETECTOR UNIT AND A MEASUREMENT METHOD FOR MEASURING A PROPERTY OF AN OBJECT

(71) Applicant: VALMET AUTOMATION OY, Espoo (FI)

(72) Inventors: Markku Mäntylä, Kangasala (FI); Pekka Suopajärvi, Oulu (FI); Jussi Tenhunen, Oulu (FI); Janne Paaso, Tyrnävä (FI)

(73) Assignee: VALMET AUTOMATION OY, Espoo (FI)

( * ) Notice: Subject to any disclaimer, the term of this patent is extended or adjusted under 35 U.S.C. 154(b) by 0 days.

(21) Appl. No.: 15/320,260

(22) PCT Filed: Jun. 24, 2015

(86) PCT No.: PCT/FI2015/050465
§ 371 (c)(1),
(2) Date: Dec. 19, 2016

(87) PCT Pub. No.: WO2015/197918
PCT Pub. Date: Dec. 30, 2015

(65) Prior Publication Data
US 2017/0160192 A1    Jun. 8, 2017

(30) Foreign Application Priority Data
Jun. 27, 2014  (FI) ...................................... 20145625

(51) Int. Cl.
*G01N 21/3559*    (2014.01)
*G01N 33/34*    (2006.01)
(Continued)

(52) U.S. Cl.
CPC ......... *G01N 21/3559* (2013.01); *D21F 7/003* (2013.01); *G01J 3/108* (2013.01);
(Continued)

(58) Field of Classification Search
CPC ....... G01N 21/3559; G01N 33/34; G01J 3/26; G01J 3/2803; G01J 3/108; G01J 3/461;
(Continued)

(56) References Cited

U.S. PATENT DOCUMENTS 3,661,462 A    5/1972  Natens
3,973,849 A *  8/1976  Jackson ................... G01J 3/02
                                                   356/320
(Continued)

FOREIGN PATENT DOCUMENTS

CN    103488025 A    1/2014
DE    199 12 500 A1  9/2000
(Continued)

OTHER PUBLICATIONS

Jun. 6, 2017 Supplementary Search Report issued in European Patent Application No. 15 81 1997.

(Continued)

*Primary Examiner* — Michael P LaPage
(74) *Attorney, Agent, or Firm* — Oliff PLC

(57) ABSTRACT

Optical multi-channel measurement unit for a process measurement includes first ends for receiving optical radiation from the optical radiation source, and second ends for outputting the optical radiation for illuminating the at least one object. Optical detectors receive optical radiation from at least one measurement channel via at least one optical filter and convert an intensity of the optical radiation to an electrical signal. A movement mechanism causes, for filtering the wavelengths of the optical radiation propagating between detectors and the optical measurement channels
(Continued)

through the optical filters, at least one of the following: movement inside at least one optical filter and movement between the filters and the detectors.

14 Claims, 4 Drawing Sheets

(51) Int. Cl.
| | |
|---|---|
| *G01N 21/89* | (2006.01) |
| *D21F 7/00* | (2006.01) |
| *G01J 3/10* | (2006.01) |
| *G01N 21/86* | (2006.01) |
| *G01J 3/12* | (2006.01) |
| *G01J 3/26* | (2006.01) |

(52) U.S. Cl.
CPC ....... *G01N 21/8903* (2013.01); *G01N 33/346* (2013.01); *G01J 3/26* (2013.01); *G01J 2003/1213* (2013.01); *G01N 2021/8663* (2013.01)

(58) Field of Classification Search
CPC ........ G01J 3/51; G01J 3/513; G01J 2003/516; D21F 7/003
See application file for complete search history.

(56) References Cited

U.S. PATENT DOCUMENTS

| | | | |
|---|---|---|---|
| 4,061,428 A * | 12/1977 | Amano | G01J 3/02 356/404 |
| 4,123,172 A * | 10/1978 | French | G01N 21/255 356/323 |
| 4,134,683 A | 1/1979 | Goetz et al. | |
| 4,345,840 A * | 8/1982 | Goetz | G01J 3/02 250/339.11 |
| 4,477,190 A | 10/1984 | Liston et al. | |
| 5,373,182 A | 12/1994 | Norton | |
| 6,060,677 A | 5/2000 | Ulrichsen et al. | |
| 6,743,337 B1 | 6/2004 | Ischdonat | |
| 2002/0197728 A1 | 12/2002 | Kaufman et al. | |
| 2003/0047135 A1 | 3/2003 | Kansakoski et al. | |
| 2003/0222219 A1 | 12/2003 | Almi et al. | |
| 2005/0134854 A1 | 6/2005 | Aguirre et al. | |
| 2006/0050277 A1 | 3/2006 | Ok et al. | |
| 2006/0132787 A1 | 6/2006 | Mestha et al. | |
| 2007/0153281 A1 * | 7/2007 | Gordon | G01J 3/36 356/419 |
| 2009/0068747 A1 | 3/2009 | Iten | |
| 2011/0007313 A1 | 1/2011 | Haran et al. | |
| 2013/0284900 A1 | 10/2013 | Freese et al. | |
| 2014/0071451 A1 | 3/2014 | Juuti et al. | |

FOREIGN PATENT DOCUMENTS

| | | |
|---|---|---|
| DE | 103 18 767 A1 | 12/2004 |
| EP | 0 953 838 A1 | 11/1999 |
| JP | H03-10146 A | 1/1991 |
| WO | 85/03575 A1 | 8/1985 |
| WO | 96/06689 A2 | 3/1996 |
| WO | 2011/135179 A1 | 11/2011 |

OTHER PUBLICATIONS

Jan. 18, 2017 Office Action issued in Finnish Patent Application No. 20145625.
Jan. 29, 2015 Search Report issued in Finnish Patent Application No. 20145625.
Oct. 16, 2015 International Search Report issued in International Patent Application No. PCT/FI2015/050465.
Sep. 21, 2016 International Preliminary Report on Patentability issued in International Patent Application No. PCT/FI2015/050465.

* cited by examiner

OPTICAL MULTI-CHANNEL MEASUREMENT UNIT, OPTICAL MULTI-CHANNEL DETECTOR UNIT AND A MEASUREMENT METHOD FOR MEASURING A PROPERTY OF AN OBJECT

FIELD

The invention relates to optical multi-channel measurement unit, optical multi-channel detector unit and a measurement method related thereto.

BACKGROUND

In the prior art, spectroscopic multi-channel measurements are based on imaging spectrometers. For example, shortwave near infrared measurements which may be done in conjunction with manufacturing process of paper or corrugated cardboard and which are made for providing information about moisture and/or other properties, may utilize imaging spectroscopy. However, the imaging spectroscopic measurement set-up is structurally and technically complicated. Additionally, cameras for the imaging spectroscopy are non-linear in response, their commercial availability is poor and potentially available ones are expensive. Furthermore, all measurement channels have common parameters such as amplification and dynamic range irrespective of the qualities or levels of the signals in the measurement channels.

Hence, there is a need to improve the optical multi-channel measurements.

BRIEF DESCRIPTION

The present invention seeks to provide an improvement in the optical multi-channel measurements. According to an aspect of the present invention, there is provided an exemplary optical multi-channel detector unit.

The invention has advantages. The measuring heads that receive optical radiation from the measured object can be made compact and structurally and technically simple. The same also applies to the heads that illuminate the measured object which results in small and economical probes with high environmental tolerance.

LIST OF DRAWINGS

Example embodiments of the present invention are described below, by way of example only, with reference to the accompanying drawings, in which FIG. 1 illustrates an example of an optical multi-channel measurement unit;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

In the infrared spectroscopy, the spectrum may be analysed on the basis of discrete optical bands or a continuous spectrum. Discrete optical bands may be generated with pass band filters which filter optical radiation of potentially continuous spectrum side or with sources of optical radiation which radiate one or more discrete optical bands. The filters typically reside on the detector side but they may reside also on the source side. Sources of discrete optical bands may comprise lasers and leds, for example. Full spectrum may be dispersed to separate wavelengths or wavelength band with gratings or prisms. The wavelengths may then be separately analysed. In Fourier transform infrared spectroscopy (FTIR), a wide range of wavelengths may be collected and analysed simultaneously. Acousto-optical infrared analysers have also been used in optical measurements. However, all of the full spectrum analysers are complicated and often also expensive.

Optical radiation may refer to electromagnetic radiation the wavelength range of which extends from ultraviolet about 100 nm to far infrared about 1000 µm, for example. The visible light may be considered to range from red about 400 nm to purple/violet about 750 nm. The range of the infrared light may be from about 750 nm to about 1000 µm. The short wave infrared light can be considered range from about 1000 nm to about 2500 nm.

Figure 1:
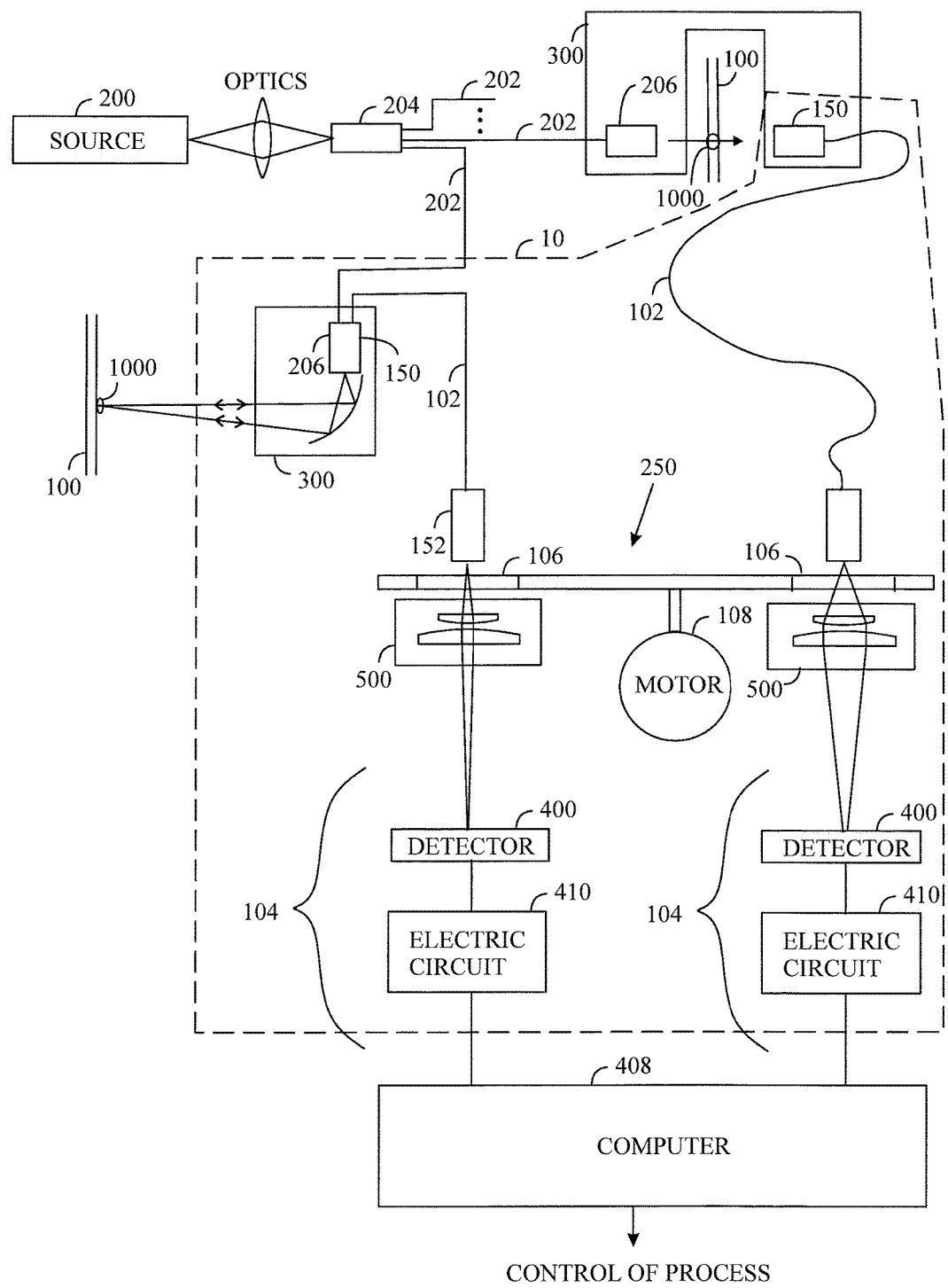

FIG. 1 presents an optical multi-channel measurement unit for measuring at least one property of at least one object 100. In an embodiment, the object 100 may comprise a sheet or a sheet-like structure. The sheet may be formed during a manufacturing process of paper or board. In an embodiment, the object 100 may comprise paper or board. In an embodiment, the sheet of paper or board may be further processed. The further processing may refer to surface treatment, corrugation or the like. The object to be measured may be a liner or a fluting in a corrugation process.

In an embodiment, the object 100 may comprise at least one layer. In an embodiment, the at least one layer may comprise glue, polymer, plastic or paste, for example. In an embodiment, the glue, polymer, plastic or paste may be or may have been applied on a surface of paper or board.

In an embodiment, the object 100 may comprise one or more biomaterials or biofuel materials. In an embodiment, the object 100 may comprise coal. In an embodiment, the object 100 may comprise may waste. In an embodiment, the object 100 may comprise chips, such as chips of wood or other plants. In an embodiment, the object 100 may comprise peat. In an embodiment, the object 100 may comprise mining and constructions materials such as rock, ore, gravel, ores, sand, soil, concrete, asphalt or any of their combination.

In an embodiment, there is one object 100 or one kind/type of object 100 to be measured.

In an embodiment, different fractions of biomaterials or biofuel materials may be carried on different conveying belt or the like. Then at least two different measurement channels 102 may be used to detect the materials on different conveying belts.

In an embodiment, the object 100 may then be measured in different phases of a process such as a paper manufacturing process of corrugated paper or a drying process of a combination of wood chips and peat, for example. The object 100 may be measured in a similar manner when it is question of the glue, plastic or paste.

In an embodiment, the object 100 or a part of the objects 100 may refer to a product produced in a process.

In an embodiment, the object 100 or a part of the objects 100 may refer to a part of a machine producing a product. In such a case, the object 100 may comprise a conveyer belt, a roll, a wire, an actuator or the like, for example, which may carry, feed, and/or modify the shape or property of the product produced.

The optical multi-channel measurement unit comprises at least one optical radiation source 200 and a plurality of source channels 202. The optical radiation source 200 may radiate at least in the measured optical spectrum and in a non-linear case the optical energy output by the optical radiation source 200 may generate the measured optical radiation. First ends 204 of the plurality of source channels 202 receive optical radiation from the optical radiation source 200 for transmitting the optical radiation to second ends 206 of the plurality of source channels 202. The second ends 206 then output the optical radiation for illuminating the at least one object 100 in a plurality of positions in the process. The plurality of measurement channels 102 then transmit the received optical radiation from the at least one object 100 in plurality of positions to the detectors 104 of the multi-channel detector unit 10.

In an embodiment, the optical source channels 202 may comprise optical fiber cables for transmitting the radiant power. In an embodiment, the optical source channels 202 may comprise terminating lenses for gathering the optical radiation emitted by the optical radiation source 200, and/or converging, collimating or diverging the optical radiation output by the optical source channels 202. The terminating lenses may be formed directly on the ends of the fiber cables or the lenses may be separate from the fiber cables. In an embodiment, the optical source channels 202 may comprise at least one mirror for guiding the optical radiation. Additionally, the optical source channels 202 may comprise at least one lens. Alternatively or additionally, other optical guides may be used.

The optical multi-channel measurement unit comprises an optical multi-channel detector unit 10 which comprises a plurality of optical measurement channels 102. The first ends 150 of the measurement channels 102 receive the optical radiation passed through, scattered, reflected and/or emitted from the measured object 100. In this manner, the second ends 206 of the optical source channels 202 and the first ends 150 of the measurement channels 102 may be on the same side of the object 100 and/or on the different side of the object 100. The different side may be an opposite side of the object 100. The measurement channels 102 transmit the optical radiation received from the at least one object 100 to optical filtering and detection.

In an embodiment, the optical measurement channels 102 may comprise optical fiber cables for transmitting the radiant power in a similar manner as the optical source channels 202. In an embodiment, the first ends 150 of the optical measurement channels 102 may comprise terminating lenses for gathering the optical radiation reflected, scattered or emitted by the at least one object 100, and/or converging, collimating or diverging the optical radiation output by second ends 152 of the optical measurement channels 102. The terminating lenses may be formed directly on the ends of the fiber cables or the lenses may be separate from the fiber cables. In this application, the optical fiber cable may refer to a single optical fiber or a bundle of optical fibers.

The optical multi-channel detector unit 10 comprises a plurality of optical detectors 104. In an embodiment, the optical multi-channel detector unit 10 comprises a plurality of optical measurement-channel-specific detectors 104. Each detector 104 receives optical radiation from at least one optical measurement channel 102 and converts intensity of the optical radiation to an electrical signal. In an embodiment, one detector 104 and one optical measurement channel 102 may be paired and optically directed to each other. In an embodiment, the detectors 104 may detect short wave infrared radiation the wavelength of which may be about 1 µm to 2.5 µm. In an embodiment, at least one detector 104 among the infrared detectors may alternatively or additionally detect visible light, too. In an embodiment, the optical fibers may be made of quartz in order to properly transmit short wave infrared light for up to tens of meters.

In an embodiment, the detectors 104 may comprise detector elements 400 such as operationally separate photo diodes. In an embodiment, the photo diodes may comprise PIN or avalanche diodes. In an embodiment, the infrared photo diodes may comprise a germanium-type of detector. In an embodiment, the infrared photo diodes may comprise indium-gallium-arsenic (InGaAs) diodes. In an embodiment, the at least one visible light photo diode may comprise gallium-arsenic-phosphorus (GaAsP) detector or a silicon-type detector. The detector elements 400 are not restricted to these or these kinds of photo diodes.

In an embodiment, the detector elements 400 may be non-overlapping pixels of a detector array in a row form (one dimensional detector structure) or in a matrix form (two dimensional detector structure). Each of the detector elements 400 may comprise one or more detecting pixels.

The optical multi-channel detector unit 10 comprises a plurality of optical filters 106 which may be placed or positioned in an optical path between detectors 104 and the optical measurement channels 102.

The optical multi-channel detector unit 10 comprises a movement mechanism 108 which causes movement in conjunction with the optical filters 106. The movement then alters filtering of the wavelengths of the optical radiation propagating from the optical measurement channels 102 to the detectors 104 through the optical filters 106.

Figure 2:
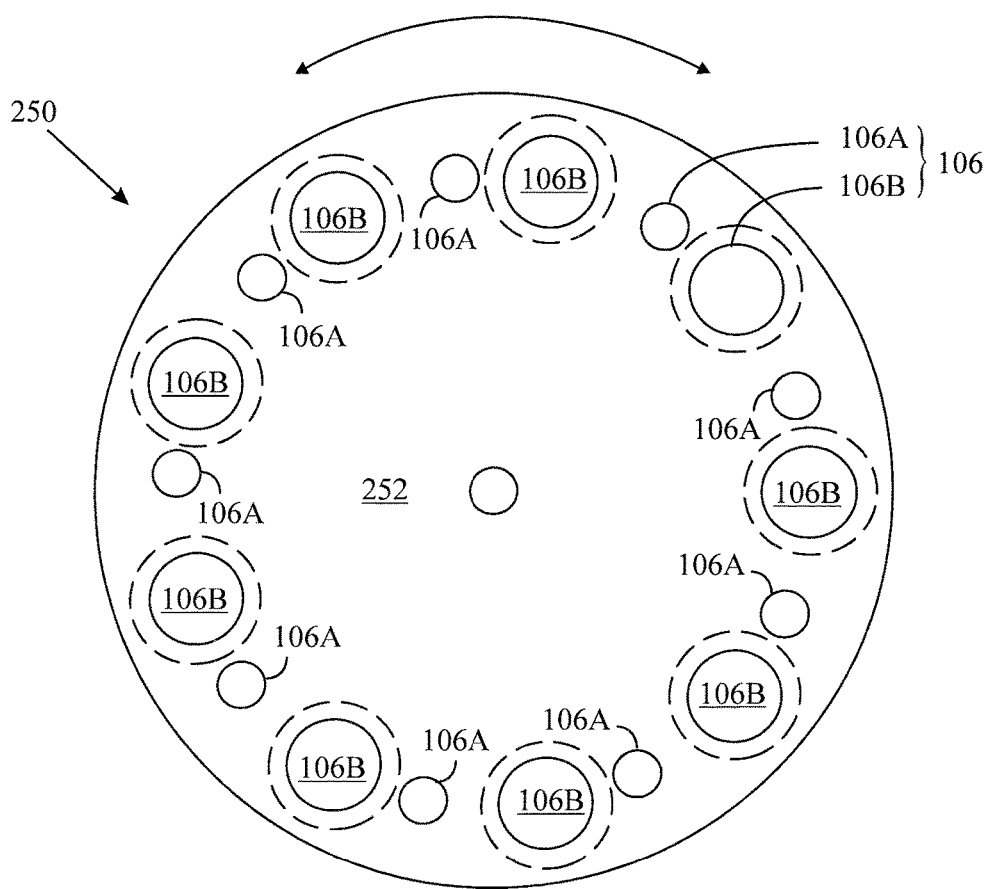
FIG. 2 illustrates example of a filter structure.

FIG. 2 shows a possible filter structure 250. In an embodiment, the filter structure 250 may comprise a disc shaped substrate 252 which has the plurality of filters 106, 106A, 106B circumferentially arranged in the disc. In an embodiment, the circumferentially arranged filters 106 may be in a form of one or more nested circles. The substrate may be of metal or plastic, for example. The material of the substrate may not be of high importance, however.

In an embodiment, a plurality of filters 106 comprise at least one spectral distribution altering filters 106B for measuring a specific feature of the at least one object 100, and at least one neutral filter 106A for measuring reference level of the object 100. The neutral filter or a grey filter is an optical filter which doesn't alter the relative spectral distribution of the intensity of the optical radiation. In an embodiment, the neutral filter may comprise or may be an empty aperture. The empty aperture may be much smaller than the spectral distribution altering filters 106B which alter the relative spectral distribution of intensity of the optical radiation. In an embodiment, the neutral filter may comprise a neutral density filter which attenuates all wavelengths the same amount. In an embodiment, on average every second filter 106 is a neutral filter 106A. In this manner, a neutral filter 106A may reside between two spectral distribution altering filters 106B.

When the intensity of the optical radiation received from object 100 is measured through the neutral filter 106A, a potential intensity change of the received optical radiation due to one or more disturbances can be eliminated from the measurement. A disturbance may be a distance variation between the object 100 and a first end 150 of a measurement channel 102, for example. Other disturbances, effects of which can be eliminated in this manner, may be caused by dust or other dirt, instability of the source 200 of the optical radiation, environmental optical noise etc. If on average every second filter 106 is a neutral filter 106A, intensity variation may be measured through the neutral filters 106A so frequently or so close to the filtered measurement made by the spectral distribution altering filters 106B that the disturbances may be effectively eliminated.

The spectral distribution altering filters 106B may be used to measure at least one of optical bands of paper or board, each optical band including only one of the following wavelengths: 1300 nm, 1450 nm, 1520 nm, 1600 nm, 1700 nm, 1810 nm, 1940 nm, 2050 nm and 2110 nm. The values may be exact values or about values.

A purpose of measurements may be to determine at least one property of the at least one object 100. A purpose of measurements may be to determine a value associated with moisture content or dryness of the object 100 of paper or board because cellulose or water has specifically high absorbance at certain wavelengths. In an embodiment, the purpose may be to measure the ratio between cellulose and water or cellulose and moisture. The measurement of moisture, dryness or ratio of cellulose and water using measured intensities of the above optical bands is known per se.

The wavelengths 1300 nm, 1520 nm may be used to measure a reference particularly when measuring water, cellulose and/or polymer. Water has strong specific absorption in optical bands including 1450 nm or about 1450 nm and/or 1940 nm or about 1940 nm and that is why such optical bands may be used to detect moisture and determine moisture content. The optical band of 2110 nm or about 2110 may be used for detection and/or determination of fiber or cellulose material. Optical bands outside the attenuation peaks of water and cellulose/fibers such as 1600 nm or about 1600 nm may be used to detect and determine baseline attenuation. The wavelengths 1600 nm and 1700 nm may be used for measuring features of polymers because polymers may have a strong absorption at a range about 1600 nm to 1700 nm. The wavelength 1810 nm may be used as reference for water because the absorption of water is weak at about 1800 nm. The wavelengths 2050 nm, 2200 nm and 2250 nm may be used as reference. The baseline attenuation may be used for determining the relative strength of attenuation of water and/or cellulose/fibers with respect to total attenuation of the object 100. Additionally, the spectral tilt of the baseline as a function of wavelength may be determined with values of attenuation in optical bands outside the attenuation peaks of water and fiber or cellulose material.

In an embodiment, the movement mechanism 108 may comprise an electric motor, for example, which may rotate the filter structure 250 such that each filter 106 will be at least momentarily between all pairs of measurement channels 102 and detectors 104 which are optically directed to each other.

In an embodiment, a certain measurement channel 102 and a certain detector 104 may be fixed pairs which are optically directed to each other.

In an embodiment, a certain measurement channel 102 and a certain detector 104 may be directed to each other at one moment. At another moment, a different measurement channel 102 and said certain detector 104 may be directed to each other. In this manner, the measurement channels 102 and the detectors 104 may move with respect to each other.

In an embodiment, the movement mechanism 108 may rotate the detectors 104 or the detector elements 400 with respect to the filters 106. In general, the movement mechanism 108 causes movement between the detectors 104 or detector elements 400 and the filters 106.

In an embodiment, the rotation may be performed in one direction only. In an embodiment, the rotation may be performed back and forth. In an embodiment, the disc of filters 106 may rotate about 1000 rpm to 6000 rpm (revolutions per minute), for example. Then one rotation may take about 60 ms to 10 ms. If the ratio of the diameter of the disc of the filter structure 250 and an average diameter of the filters is 10 mm and there are 10 filters 106 at least almost side by side, then it can be estimated that a measurement with one filter 106 may take about 6 ms to 1 ms. In an embodiment, several measurement results filtered similarly may be combined in order to form an average result. In an embodiment, all measurements may be integrated over about 1 second, for example. That is, each result may be based on an average of about 150 to 1000 individual measurement results, for example.

Figure 3:
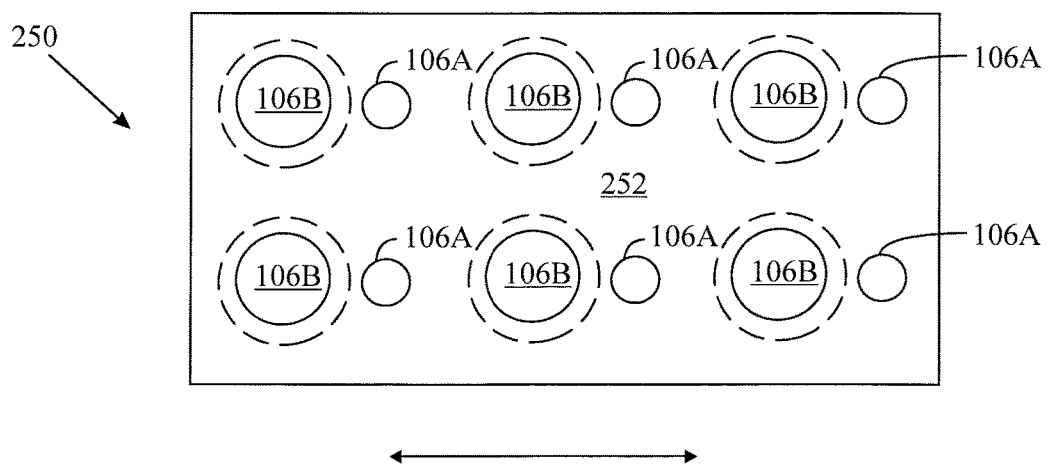
FIG. 3 illustrates of an example of another filter structure.

In an embodiment shown in FIG. 3, the filter structure 250 may have substrate 252 which has a shape of a rectangle and the filters 106 may be in one or more rows in the substrate 252. In an embodiment, the movement mechanism 108 may move the rectangular filter structure 250 back and forth such that filters 106 may visit between every pairs of measurement fibers 102 and detectors 104 one after another.

In an embodiment, the filters 106, 106B may comprise interference filters. The interference filters may operate as notch filters such that they pass a narrow band of wavelengths of the optical radiation through to the detectors 106. A bandwidth of the interference filters may be narrower than about 10 nm, for example. However, the bandwidth of the filters 106 is not limited to the about 10 nm.

In an embodiment, at least one filter 106, 106B may comprise Fabry-Perot interferometer which may also be considered as one kind of an interference filter. The Fabry-Perot interferometer operates such that optical radiation is made to bounce back and forth multiple times between two reflecting plates. Constructive interference of the optical radiation depends on the distance of the reflecting plates, and the wavelengths which have the constructive interference will pass the Fabry-Perot interferometer. Often the wavelength band which is of interest is so narrow or otherwise so controlled that only one wavelength of the optical radiation will in principle pass the Fabry-Perot interferometer. By changing the distance between the reflecting plates it is possible to form an adjustable etalon filter of a Fabry-Perot type. Then it is easy to adjust each filter to at least one state where it passes at least one desired wavelength to the detector 106. In an embodiment, the adjustment may be continuous as a function of time. Thus, it is possible to make the Fabry-Perot type filters 106B to scan over a desired optical band. The scanned optical band may be scanned discretely or continuously. The scanned optical band may include at least one wavelength of infrared light and possibly also at least one wavelength of visible light.

In the embodiment of the Fabry-Perot type solution, the filters 106 need not necessarily be made to move from one pair of a measurement fiber 102 and a detector 104 to another, but the movement mechanism 108 may comprise an actuator for moving at least one plate of the two reflecting plates set parallel to each other in the Fabry-Perot interferometer. This movement may cause the optical distance of the plates inside the filter 106 of the Fabry-Perot interferometer to change which, in turn, shifts a wavelength of an optical band passing through to the detector(s) 104. In the embodiment, the movement mechanism 108 may comprise a piezo electric actuator or an electrostatic actuator, for example. The energy for piezo or electrostatic movement may be fed to the filter structure 150 inductively.

Figure 4:
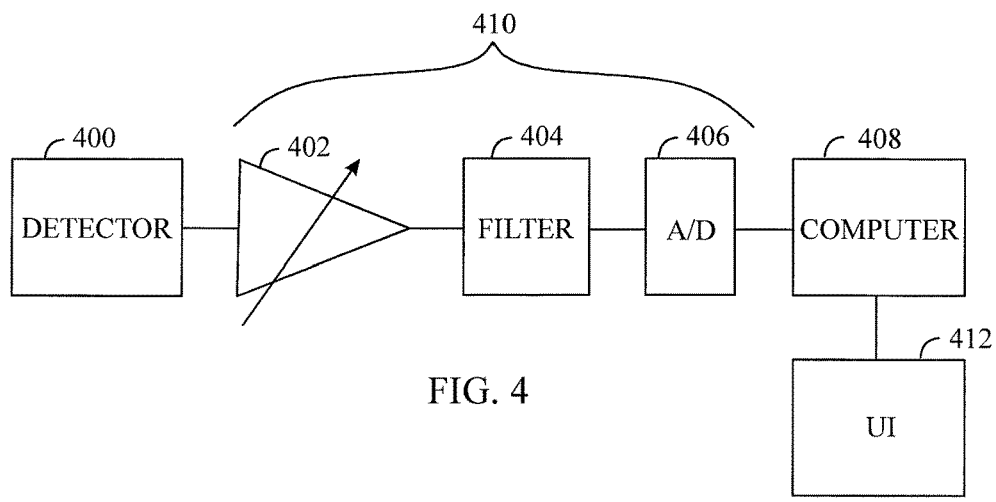
FIG. 4 illustrates an example of an electric circuit.

In an embodiment shown in FIG. 4, each optical detector 104 comprises or is coupled with at least one detector element 400 and an electrical circuit 410 which may have an amplifier 402 for amplifying the analog signal output by the at least one detector element 400. In this manner, each measurement channel may be made independent from other channels also electrically. Different detector elements 400 may need different amplification. Additionally, the electric signals may be filtered detector-element-specifically in filter circuit 404 of the electric circuit 410. The filter circuit 404 may be a part of at least one optical detector 104. In an embodiment, the filter circuit 404 may be a part of at least one measurement-channel-specific optical detector 104. Finally, each analog signal may be converted into a digital form in a A/D converter 406 of the at least one optical detector 104 for a computer based signal processing in at least one processing unit 408. The computer including the at least one processing unit 408 may also comprise a user interface 412 for accepting user input and for presenting the measurement results in a visual or audio form. The visual form may include graphical and or symbolic representation. The symbolic representation may include alphanumeric symbols and/or other signs of one or more writing systems.

In an embodiment, the detectors 104 may be dynamically adjustable. In an embodiment, the dynamically adjustable detectors 104 may be adjustable on the basis of at least one of the following: amplification and integration time.

In an embodiment, the amplification of amplifiers 402 of the detectors 104 may be electrically controllable. In an embodiment, the amplification of the amplifier 402 may be controlled by a user. In an embodiment, the amplifier 402 may have an automatic gain control such that the amplification is always at optimum.

In an embodiment, the integration time of the detectors 104 may be controlled by altering the period of time during which the detector elements 400 generate electric charge in response to optical radiation the detector elements 400 receive for to be output as electric currents. The longer the integration time, the less thermal noise of the detector elements 400 has effect to the output electric currents, for example. The integration time depends mainly on capacitance and resistance of the detector elements 400 and that is why the integration time may be modified with increase or decrease of resistance in the detector elements 400. Additionally or alternatively capacitance may be modified.

Different wavelengths of optical radiation may have different intensities. By changing the amplification, all intensities may be made to stay in the operative range of the A/D-converter, for example. By controlling the integration time, signal-noise ratio of potentially weak optical signals can be increased. However, too long integration time may result in distortion of the electric signal because the electric signal may go out of the dynamic range of the amplifier 402.

In an embodiment, each detector 104 may comprise at least one optical component 500 for gathering the optical radiation coming from the measurement channel 102 to the detector 104. In an embodiment, each detector 104 may comprise at least one measurement channel-specifically dimensioned optical component 500. The optical component 500 may comprise at least one lens. The optical component 500 may be collimating or converging.

A plurality of measurement points 1000 in one or more objects 100 may be measured through the filters 106 in a common filter structure 250. In an embodiment, even the physical filters 106 may be common to all measurement channels 102 when the filter structure rotates or moves back and forth. The spectral data is produced on the basis of mechanical movement associated with the filters 106. Either are the filters 106 made to move successively from a gap between one pair of a measurement channel 102 and a detector 104 to another gap between a different pair, or the filters 106 are made to change their optical pass bands on the basis of mechanical movement therein.

In an embodiment, the multi-channel measurement unit may be applied to measure moisture content, cellulose content, ash content, basis weight, paste content/thickness of a sheet of a paper or board, brightness any of their combination or the like. The brightness may be used to determine the amount of peat in a mixture of wood chips and peat. The determined amount may be an absolute value or a relative value.

The measurement probe 300, i.e. what is associated with the second ends 206 of the plurality of source channels 202 and the first ends 150 of the measurement channels 102, can be made small in size because the probe 300 is passive without electronic components. Thus the probe 300 may be placed in narrow spaces in process machines. The probe 300 can stand wide variety of environments. For example the temperature range of the probe 300 is broad such that the probe can tolerate freezing cold and boiling hot equally well. The probe 300 and its output optical signals don't need temperature or other environmental condition compensation.

Additionally, different channels may be both optically and electronically independent up to analog-digital conversion.

Figure 5:
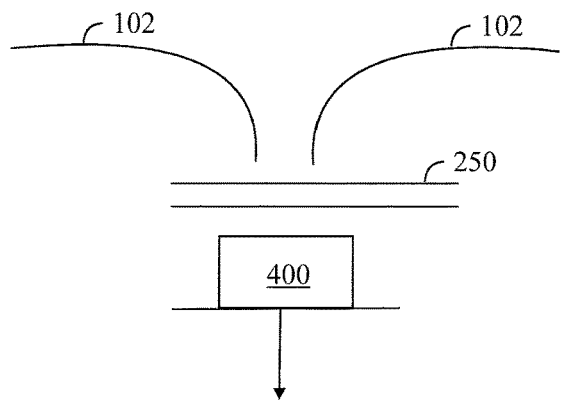
FIG. 5 illustrates an example where more than one measurement channel is directed to one detector element.

FIG. 5 illustrates an embodiment, where more than one measurement channel 102 is directed to one detector element 400. If no separation of the optical radiation is performed, the detector element 400 generates an electric signal which is a sum of the optical signals from the measurement channels 102. The sum may be understood to represent an average of the measured property.

The optical signal output by the measurement channels 102 may be separated from each other by time-division multiplexing (TDM) or frequency-division multiplexing (FDM). In time-division multiplexing, only one measurement channel 102 outputs optical radiation to the detector 400 at a time and all measurement channels 102 output optical radiations to detector successively. In frequency-division multiplexing, different measurement channels 102 output optical radiation with different multiplexing or pulsating frequencies.

In an embodiment, the measurement channels 102 may be separated from each other in the time-division multiplexing manner by causing the optical sources 200 to radiate optical radiation at different and non-overlapping moments of time, for example. Then the at least one object 100 is also illuminated at different moments at different locations of the measurement channels 102. The moments and thus measurements with different measurement channels 102 may be separated in electrical signals in the electric circuit 410 or the at least one signal processing unit 408 using analog or digital filtering.

In an embodiment, the measurement channels 102 may be separated from each other in the frequency-division multiplexing manner by causing the optical sources 200 to radiate optical radiation with different frequencies, for example. Then the at least one object 100 is also illuminated at different frequencies at different locations of the measurement channels 102. The frequencies and thus measurements with different measurement channels 102 may be separated in electrical signals in the electric circuit 410 or the at least one signal processing unit 408 using analog or digital filtering.

Figure 6:
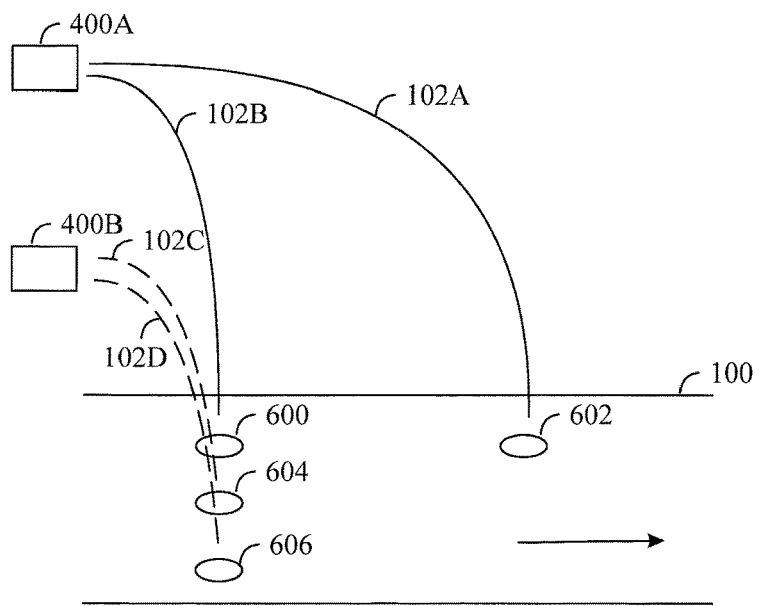
FIG. 6 illustrates an example of CD or MD measurements with one detector element.

FIG. 6 illustrates an embodiment where different cross-directions (CD) and/or machine-directions (MD) are measured using one detector element 400 for at least two measurement channels 102. In an embodiment, two machine directional locations of the object 100 such as a sheet may be measured using the summing/averaging principle, the TDM principle or the FDM principle. The measurement channels 102A and 102B receive optical radiation from the object 100 at two machine directionally different locations 600, 602 and the detector element 400A detects the optical radiation at least nearly at the same moment. In the TDM principle the detections are performed at different moments but typically the difference is so small that it may be ignored.

In an embodiment, two cross directional locations 604, 606 of the object 100 such as a sheet may be measured using the summing/averaging principle, the TDM principle or the FDM principle. The measurement channels 102C, 102D receive optical radiation from the object 100 at two cross directionally different locations 600, 602 and the detector element 400B detects the optical radiation at least nearly at the same moment. In the TDM principle the detections are performed at different moments but typically the difference is so small that it may be ignored. When using the TDM principle or the FDM principle, the measurements of the object 100 may be separated from each other.

When measuring MD and/or CD moisture of the object 100, it may be possible to monitor the drying of the object 100, and on the basis of monitoring the drying process it is also possible to control the drying process.

Figure 7:
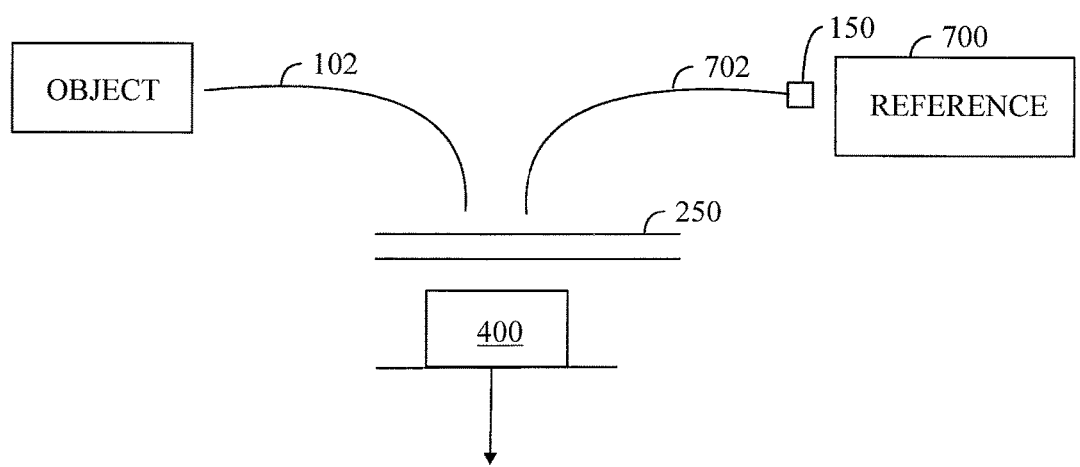
FIG. 7 illustrates an example of measurement with a reference using at least two measurement channels and one detector element.

FIG. 7 illustrates an embodiment where a measured spot of the object 100 and its reference 700 are measured with at least two measurement channels 102, 702 and one detector element 400. The measurement channel 702 of the reference 700 may be similar to the measurement channels 102 of the object 100. The reference 700 has a known spectrum.

Similarly to the measurement channel 102, the second end 206 of the optical source channels 202 and the first end 150 of the measurement channels 702 may be on the same side of the reference 700 or on the different side of the reference 700. Thus, the reference 700 may be measured using a pass-through measurement or a reflection measurement which are the same configurations as with the object 100.

In an embodiment, the measurement of the object 100 and the reference 700 may be measured using the summing/averaging principle, the TDM principle or the FDM principle for the intensity of the optical radiation received from the measurement channels 102, 702. When using the TDM principle or the FDM principle, the measurement of the object 100 and the reference 700 may be separated from each other. The reference measurement may be used to correct the measurement of the object 100.

In general, the measured results may be used in process control.

Figure 8:
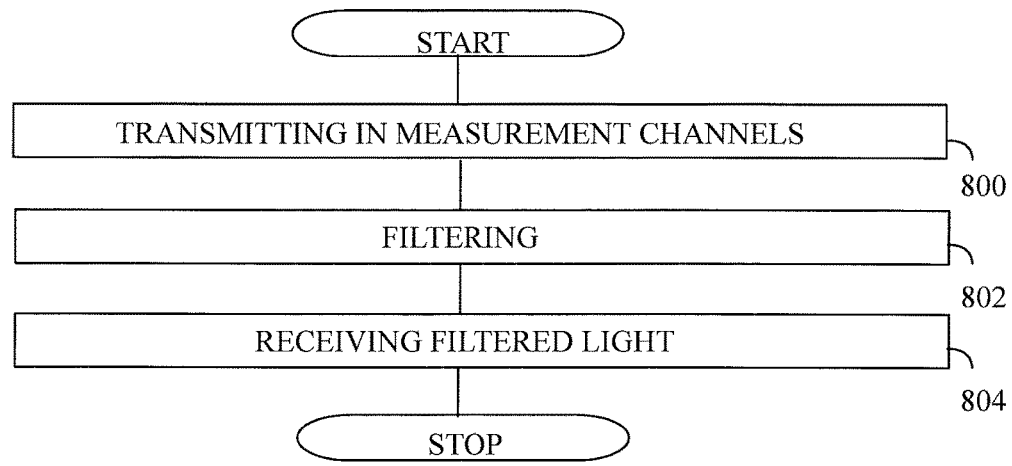
FIG. 8 illustrates of an example of a flow chart of a measuring method.

FIG. 8 is a flow chart of the measurement method. In step 800, optical radiation received from the at least one object 100 is transmitted by a plurality of optical measurement channels 102. In step 802, wavelengths of the optical radiation are filtered when propagating between a plurality of optical detectors 104 and the optical measurement channels 102 through optical filters 106 by causing at least one of the following by a movement mechanism 108: movement inside at least one optical filter 106 and movement between the filters 106 and the detectors 104. In step 804, optical radiation is received with each detector element 400 of a plurality of optical detectors 104 from at least one optical measurement channel 102 via the at least one optical filter 106 and intensities of the optical radiation detected by the plurality of optical detectors 104 are converted to electrical signals.

The method shown in FIG. 8 may be implemented as a logic circuit solution or computer program. The computer program may be placed on a computer program distribution means for the distribution thereof. The computer program distribution means is readable by a data processing device, and it encodes the computer program commands, carries out the measurements and optionally controls the processes on the basis of the measurements.

The distribution medium, in turn, may be a medium readable by a data processing device, a program storage medium, a memory readable by a data processing device, a software distribution package readable by a data processing device, a signal readable by a data processing device, a telecommunications signal readable by a data processing device, or a compressed software package readable by a data processing device.

It will be obvious to a person skilled in the art that, as technology advances, the inventive concept can be implemented in various ways. The invention and its embodiments are not limited to the example embodiments described above but may vary within the scope of the claims.

The invention claimed is:

1. An optical multi-channel measurement unit for measuring moisture or dryness of paper or board during manufacture or further processing thereof, wherein the multi-channel measurement unit comprises:

a first source channel and a second source channel, both the first source channel and the second source channel defining first ends and second ends, the second end of the first source channel being configured to illuminate a first location on the paper or board with optical radiation from an optical radiation source and the second end of the second source channel being configured to illuminate a second location on the paper or board with optical radiation from the optical radiation source, the first location being directionally different than and spaced apart from the second location;

a first optical measurement channel and a second optical measurement channel, both the first optical measurement channel and the second optical measurement channel comprising optical fiber cables and the first optical measurement channel being configured to transmit infrared optical radiation received from the first location on the paper or board and the second optical measurement channel being configured to transmit infrared optical radiation received from the second location on the paper or board;
a first infrared optical filter and a second infrared optical filter;
a first optical detector and a second optical detector, the first optical filter being in a first optical path between the first optical measurement channel and the first optical detector, the second optical filter being in a second optical path between the second optical measurement channel and the second optical detector, the first optical detector being paired with and optically directed to the first optical measurement channel, the second optical detector being paired with and optically directed to the second optical measurement channel;
the first optical detector being configured to receive infrared optical radiation from the first optical measurement channel via the first optical filter and the second optical detector being configured to receive infrared optical radiation from the second optical measurement channel via the second optical filter to convert an intensity of the optical radiation to an electrical signal; and
a movement mechanism configured to move the first optical filter from between the first optical measurement channel and the first optical detector to between the second optical measurement channel and the second optical detector and to simultaneously move the second optical filter from a first position to a second position so as to: (i) filter the wavelengths of the infrared optical radiation propagating between the optical detectors and the optical measurement channels through the optical filters, (ii) measure water only at one or more specific absorption bands, the movement of the first optical filter and the second optical filter being configured to cause the first optical filter to be between the first optical measurement channel and the first optical detector momentarily, and the second optical filter to be between the second optical measurement channel and the second optical detector momentarily.

2. The multi-channel measurement unit of claim 1, wherein the first optical filter and the second optical filter each comprises at least one spectral distribution altering filter for measuring a specific feature of at least one object and at least one neutral filter for measuring a reference level.

3. The multi-channel measurement unit of claim 1, further comprising a multi-channel detector unit that includes a filter structure including a substrate, the first optical filter, and the second optical filter, wherein the movement mechanism is configured to move the first optical filter and the second optical filter from the first optical measurement channel and first optical detector to the second optical measurement channel and the second optical detector.

4. The multi-channel measurement unit of claim 1, wherein the first optical measurement channel and the second optical measurement channel are configured to receive optical radiation from at least one object that is sheet-shaped.

5. The multi-channel measurement unit of claim 1, wherein the electrical amplifying circuit is dynamically adjustable.

6. The multi-channel detector unit of claim 5, wherein the electrical amplifying circuit is dynamically adjustable based on at least one of amplification and integration time.

7. The multi-channel measurement unit of claim 1, wherein the electrical amplifying circuit is dynamically adjustable based on at least one of amplification and integration time.

8. The multi-channel measurement unit of claim 1, wherein the first optical detector and the second optical detector each comprises at least one measurement channel-specifically dimensioned optical component for gathering the optical radiation coming from the first measurement channel and the second measurement channel to the first optical detector and the second optical detector, respectively.

9. The multi-channel measurement unit of claim 1, wherein at least one of the first optical measurement channel and the second optical measurement channel comprises at least one optical fiber.

10. The multi-channel measurement unit of claim 1, wherein the first optical detector and the second optical detector each includes a plurality of detector elements, the first optical detector and the second optical detector are configured to measure infrared radiation and to measure visible light.

11. The optical multi-channel detector unit of claim 1, further comprising an optical multi-channel measurement unit that includes:
the optical radiation source configured to radiate an optical infrared spectrum to be measured;
the first source channel and the second source channel, the first ends of the first source channel and the second source channel being configured to receive optical radiation from the optical radiation source and the second ends of the first source channel and the second source channel being configured to output the optical infrared radiation for illuminating the paper or board in a plurality of the different positions; and
the first optical measurement channel and the second optical measurement channel being configured to transmit the received optical infrared radiation from the plurality of different positions to the first optical detector and the second optical detector.

12. An optical measuring method of moisture of paper or board during manufacture or further processing thereof for a multi-channel detector unit, the method comprising:
illuminating, by a second end of a first source channel, a first location of the paper or board with optical radiation from an optical radiation source, and illuminating, by a second end of a second source channel, a second location of the paper or board with optical radiation from the optical radiation source;
transmitting, by a first optical measurement channel and a second measurement channel comprising optical fiber cables, optical infrared radiation received from the first location and the second location of the paper or board;
moving a first optical filter from between the first optical measurement channel and the first optical detector to between the second optical measurement channel and the second optical detector and simultaneously moving the second optical filter from a first position to a second position so as to: (i) filter the wavelengths of the infrared optical radiation propagating in optical paths between the optical infrared detectors and the optical measurement channels through optical infrared filters, and (ii) measure water only at one or more specific absorption band, the movement of the first optical filter and the second optical filter being configured to cause the first optical filter to be between the first optical measurement channel and the first optical detector momentarily, and the second optical filter to be between the second optical measurement channel and the second optical detector momentarily, each of the first optical detector and the second optical detector comprising or being operationally coupled with at least one detector element and an electrical amplifier circuit for amplifying an analog signal output by the at least one detector element; and receiving, with each detector element of the first optical detector and the second optical detector, optical infrared radiation from at least one optical measurement channel via one optical infrared filter of the optical infrared filters, and converting intensities of the optical infrared radiation detected by the plurality of optical infrared detectors to electrical signals.

13. The method of claim 12, wherein each of the first optical detector and the second optical detector is paired with the first optical measurement channel and the second measurement channel, respectively.

14. The method of claim 12, the method further comprising:

receiving, by a first end of the first source channel and a first end of the second source channel, optical radiation from the optical radiation source;

outputting, by the second end of the first source channel and the second end of the second source channel, the optical radiation for illuminating at least one object in a plurality of positions.

* * * * *